(12) United States Patent
Parkhurst et al.

(10) Patent No.: US 6,528,014 B1
(45) Date of Patent: Mar. 4, 2003

(54) FOUL AIR ELIMINATOR

(75) Inventors: Stephen L. Parkhurst, Austin, TX (US); Morey E. Osborn, Cedar Park, TX (US)

(73) Assignee: SL Parkhurst Corporation, Austin, TX (US)

( * ) Notice: Subject to any disclaimer, the term of this patent is extended or adjusted under 35 U.S.C. 154(b) by 60 days.

(21) Appl. No.: 09/661,109

(22) Filed: Sep. 13, 2000

Related U.S. Application Data

(60) Provisional application No. 60/153,764, filed on Sep. 13, 1999.

(51) Int. Cl.[7] ................................................. A61L 9/00
(52) U.S. Cl. ........................... 422/5; 424/76.1; 422/122
(58) Field of Search .................... 4/213, DIG. 3, 4/300; 424/76.1, 76.7; 422/5, 122; D23/366

(56) References Cited

U.S. PATENT DOCUMENTS

| | | | |
|---|---|---|---|
| 3,337,992 A | * | 8/1967 | Tolson ....................... 4/DIG. 3 |
| 4,099,047 A | | 7/1978 | Kirkland, Jr. |
| 4,317,242 A | | 3/1982 | Stamper |
| 4,604,110 A | * | 8/1986 | Frazier ........................... 55/74 |
| 4,959,207 A | * | 9/1990 | Ueda et al. .................. 424/76.1 |
| 5,253,371 A | * | 10/1993 | Slawinski ....................... 4/213 |
| 5,488,741 A | | 2/1996 | Hunnicutt, Jr. |
| 5,800,806 A | * | 9/1998 | Yamamoto .................. 424/76.1 |

FOREIGN PATENT DOCUMENTS

| | | | | |
|---|---|---|---|---|
| EP | 331 192 | * | 9/1989 | ..................... 4/213 |
| FR | 2622228 | * | 4/1989 | ..................... 4/213 |
| JP | 56115619 A | * | 9/1981 | |

* cited by examiner

Primary Examiner—Terrence R. Till
Assistant Examiner—Sean E. Conley
(74) Attorney, Agent, or Firm—McGarry Bair LLP

(57) ABSTRACT

A converter for transforming malodorous components of foul air comprises a porous layer having an oxidizing agent and an aqueous solution of a promoter. The promoter is preferably a water-soluble ethylene oxide or propylene oxide adduct. The layer is typically used in a gas-handling system to eliminate the foul air from a toilet or a bedpan. The layer can be used alone or with a second layer of activated charcoal. A Lewis acid and/or a Lewis base can be also used with the converter.

29 Claims, 4 Drawing Sheets

FOUL AIR ELIMINATOR

This application claims the benefit of U.S. Provisional Application No. 60/153,764, filed Sep. 13, 1999.

BACKGROUND OF THE INVENTION

1. Field of the Invention

This invention is a device for removing odors from air. Specifically, the present invention relates to air cleansing during the operation of a contemporary toilet to eliminate the unpleasant odors and adventitious bacteria. More particularly, the present invention concerns retrofitting the device onto existing toilets.

2. Description of the Related Art

Since the dawning of the modern age many people have at one time or another contemplated ways to cope with or eliminate malodorous air and ammonia that arises during use of the contemporary toilet. A number of methods have been employed for this purpose. These include burning candles, use of incense, opening windows, switching on overhead fans, spraying fragrances, use of elaborate toilet bowl designs and so on. These methods are ineffective, a nuisance to implement or too costly to install. Apart from the invention described herein, a single product, which is safe, effective and economical in dealing with this problem, has not emerged. Past solutions may have acted to ameliorate foul air to a limited degree, but they did so in a circuitous fashion—by rerouting the flatus or hiding it with fragrances and the like. Previous approaches do not target the fundamental cause of the trouble. The direct method of addressing this problem lies in the chemistry associated with the malodorous components themselves.

In contrast to fecal matter, tissue fluid, blood or other bio-fluids, the body of knowledge on the biochemical events giving rise to the formation of flatus is scant. Furthermore, there is not a single source that deals with the subject in a thorough fashion. Information on the compositional aspects of flatus taken from varied sources reveals the physiology and chemistry to be relatively plain. However, eliminating its negative properties affords a challenge. Flatus arises from aerophagia (swallowed boluses of air), gas diffusion (e.g. carbon dioxide) from the blood, bacterial production in the lumen, descending and sigmoid colons and from trace quantities of non-gaseous components carried with the flatus by mass transfer during expulsion. Swallowed air accounts for a large portion of nitrogen, oxygen and carbon dioxide, while diffusion from gas gradients contributes much of the remaining carbon dioxide and nitrogen portions. Methane, hydrogen, hydrogen sulfide (as well as a small amount of mercaptan) and carbon dioxide result from bacterial fermentation of residual ingesta at the point of the lumen and at locations further down in the alimentary tract. The trace non-gases are primarily heterocyclic amines from protein-rich ingesta. Specifically, the two amino acids, proline and tryptophan can lead to pyrrole and indole (C4H5N and C8H7N respectively) derivatives subsequent to deamination/decarboxylation of the parent molecules. Nitrogen from deamination is nearly quantitatively converted to ammonia and later to urea in a formal condensation with carbon dioxide in vivo. Energy from that transformation is captured and stored in lipid form as ATP for later use in the body. The remaining moieties of the proline and tryptophan precursors are readily converted in vivo to pyrrole and indole nuclei respectively. Both of these materials are thermodynamically stable owing to their aromaticity, but this is especially germane in the case of indole and its derivatives, which are resistant to further catabolic breakdown. Its structural integrity and associated physical-chemical properties are preserved while in the body. Consequently, indole is believed to be more ubiquitous in flatus among the general population, and the only alkaloid of appreciable significance in flatus. Even so the majority of this non-gaseous component will be eliminated as-is in fecal matter rather than flatus. The only other relevant constituent in flatus is low molecular weight carboxylic acid (butyric acid for example) that is generated from enzyme hydrolysis of ester oils. Flatus components and their approximate relative abundance are depicted below.

TABLE 1

Major (and coincidentally odorless) Components of Flatus

| Flatus Concentration Constituent Range |
|---|
| Oxygen 0–10% |
| Hydrogen 5–35% |
| Methane 0–30% |
| Carbon Dioxide 5–50% |
| Total Minor Comp. (Table 2) <1% |

TABLE 2

Minor (and coincidentally malodorous) Components of Flatus

| Flatus Concentration Constituent Range (parts per million) |
|---|
| Indoles 0.5–10 ppm |
| Hydrogen Sulfide 0.5–10 ppm |
| Pyrroles <10 ppm |
| Carboxylic Acids 1–100 ppm |
| Mercaptans <0.1 ppm |
| Miscellaneous trace |

It is to be noted that there is variation in flatus for individuals between expulsions as well as variation between individuals within the general population as a whole. For example, one third of the population produces no methane. This is why only ranges for flatus components are given.

The major components (Table 1) are present at a strength that is orders of magnitude greater than the minor ones (Table 2). The sum of all minor components in flatus seldom exceeds 1%. However, the most interesting aspect of flatus composition is that there is no major component which is malodorous—and there is no minor component which is not malodorous. Thus, as it is the principal intent of this invention to eliminate the experience of foul air exposure, it was only necessary to address problems created by the minor components (Table 2), and to a lesser extent, ammonia from urination. Indoles, pyrroles, carboxylic acids and most mercaptans are not gases at ambient or in vivo conditions. These four minor components, therefore, are susceptible to capture by activated charcoal. Indeed, in prior art, cited herein, a few previous inventors have incorporated the use of activated charcoal in their apparatuses. These devices were undoubtedly successful in removing these four substances, at least to a limited degree.

On the other hand activated charcoal cannot be used to mitigate hydrogen sulfide, contrary to numerous efforts and claims of the past. The mechanism for adsorption by activated charcoal involves, in sequence, condensation, Van der Walls attraction and capillary action to the interior core of the charcoal particle, at or near the boiling point of the intended substrate. With a boiling point of less than −60° C., hydrogen sulfide cannot undergo even the first step of the adsorption process unless it is taking place under cryogenic conditions.

As ambient conditions are not conducive to this adsorption process, it would be advantageous to devise an alternative method for removing hydrogen sulfide, within the operating parameters to be found in the user environment.

SUMMARY OF THE INVENTION

The invention relates to a converter for use in a foul air eliminator. The invention further relates to the foul air eliminator comprising the converter.

The converter includes a chemically reactive component for chemically altering an odorous component of flatus. The chemically reactive component can include an oxidizing agent or an anhydride. The chemically reactive component can be drawn from the group consisting of carboxylic acid anhydrides, olefins, alkynes, carboxylic acid esters, aldehydes, isonitriles, alkyl halides, alpha diketones, acyl halides, diazo ketones, epoxides, isocyanates, isothiocyanates, thiocyanates, vinyl ethers, diazonium salts, alpha-beta unsaturated carbonyls, ketones, alpha-beta unsaturated nitriles, metal hydrides, and carbamates.

In an embodiment of the invention, the converter further comprises a component for ameliorating ammonia odor.

The chemically reactive component can further display disinfectant properties. The converter can further include a promoter to enhance the chemical conversion of flatus.

In one embodiment, the eliminator comprises a housing adapted to be supported from a toilet. In another embodiment, the eliminator comprises a housing adapted to be self-supporting.

The eliminator can further comprise a bed of activated charcoal, wherein the chemically reactive component works synergistically with the activated charcoal.

In one of its aspects, the converter can be removed when the chemical reactive component has been depleted. The eliminator can further comprise a fragrance repository.

In one of its embodiments the eliminator comprises an impeller for drawing a volume of gas through the converter. The impeller can be manually activated, or can be automatically activated, such as by a pressure actuator located under a toilet seat, by a light detector switch, or by a radio frequency detector switch.

In a further embodiment, the chemically reactive component includes a first zone including a hydrogen sulfide reactant and one of a Lewis base and a Lewis acid, and a second zone includes the other of the Lewis base and the Lewis acid. This embodiment can further include an activated charcoal zone. The zones can be formed as layers within the converter. The layers can further comprise a membrane for suspending the chemically reactive components.

In a further embodiment, the converter comprises a packed column containing porous beads impregnated with the chemically reactive components.

DESCRIPTION OF THE PREFERRED EMBODIMENT

This invention includes two sub-units. The first sub-unit is referred to herein as the "converter" (or "converting system"). It is that part of the device, which contains the agents that chemically change ammonia from urination and odoriferous components in flatus to non-malodorous substances. The second sub-unit is referred to herein as the "gas-handler" (or "gas-handling system"). It delivers the foul air to the converter for alteration and discharges the malodor-free air that results. In addition, the two systems are integrated in a manner that introduces efficiency to the overall process.

1. Converter

Figure 1:
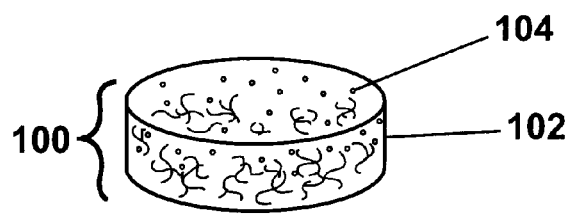
FIG. 1 is a perspective view of a converter element with an oxidizing agent according to the invention.

Referring to FIG. 1 at the heart of the invention is a converter 100. It generally consists of a zone of the agent used for the chemical conversion of the odor causing substances. In the depicted embodiment of FIG. 1, flexible fabric 102 is impregnated with an agent 104, or agents. The fabric must be chemically resistant to the conversion agent, or agents, and porous enough to allow the air stream delivered by the gas-handler to smoothly pass through it (0.1 SCFM or higher) when making contact with the converter chemical. It is essentially a membrane that is positioned in the converter in such a way that the foul air can not escape without first making contact with the agent.

The area of the incident surface varies. For example, effective bathroom models have had areas of two to six square inches. The surface area can be larger in units that have more demand, such as a hospital unit (see FIG. 7). A variation of this membrane design is a packed column containing beads impregnated with converter agent. In either case the foul air is forced to make contact with chemical agents in the converter. The converter is a modular unit that can be easily removed and replaced when needed.

Hydrogen sulfide and, to a lesser extent, mercaptans, are the only odor-causers, other than ammonia from urination, that require chemical conversion. The other malodorous components can be dealt with in a manner well known in the art. The sulfur compounds are transformed into non-volatile and non-odorous compounds when they are reacted with various oxidizers. Therefore, in its simplest form the conversion chemical may consist only of an oxidizing agent—particularly if removing hydrogen sulfide is the only objective. This simplest approach does in fact have merit. The reason is that hydrogen sulfide is the most egregious of the malodorous components. It is toxic and detectable by the human olfactory system at extremely low levels (typically parts per billion). Moreover, current theory on nerve receptor site mechanics holds that both primary and secondary receptor nerves are capable of detecting multiple numbers of different substances, and that in order for a nuisance odor to be experienced, a certain threshold number of these sites must be triggered directly or indirectly. It may well be that for most of the population, simply eliminating the odor owing to the hydrogen sulfide could sufficiently reduce the total impact of the entire group of malodorous components, so that the nuisance threshold is not reached. This would mean a commercial goal of eradicating the unpleasant experience could be achieved by using only an oxidizing agent in this device in most instances. Thus, at a minimum, the converter fabric has a single oxidizing agent applied to it.

For daily use on a given commode over a three month period, the minimum quantity of oxidizing agent required for effective operation of this invention varies from 0.1 grams to 10 grams depending on the molecular weight, particle size and reactivity of the oxidizing agent used. The reason that such a small quantity of reagent is needed is that the amount of malodorous components being converted are so miniscule. Indeed, the longevity of the converter module depends more on the intramolecular degradation tendencies of the specific reagents being used than on the load level of the malodorous components during use.

In some instances the oxidizing agent must first be adsorbed on a support before impregnation on the fabric. In other cases it can be used neat—or on a support. A useful support can be any chemically resistant adsorbent material including, but not limited to, precipitated silica, fumed silica, diatomaceous earth, inert elastomeric pellets, vermiculite, natural or synthetic zeolites or alumina. Common oxidizing agents that are effective in this device are listed below (Table 3). Mixtures of these materials in different ratios are also effective.

TABLE 3

Common oxidizers useful for conversion of hydrogen sulfide.

| | |
|---|---|
| 1. | Sodium dichloroisocyanuric acid. |
| 2. | Potassium dichloroisocyanuric acid. |
| 3. | Sodium trichloroisocyanuric. |
| 4. | Potassium trichloroisocyanuric. |
| 5. | Potassium permanganate. |
| 6. | Sodium permanganate. |
| 7. | Sodium hypochlorite in wet solvent. |
| 8. | Potassium hypochlorite in wet solvent. |
| 9. | Hypochlorous acid in wet solvent. |
| 10. | Calcium oxide. |
| 11. | Magnesium oxide. |
| 12. | Chromium trioxide. |
| 13. | Manganese dioxide. |
| 14. | Chromium trioxide-pyidine complex. |
| 15. | Lead tetraacetate. |
| 16. | Barium oxide. |
| 17. | Cadmium oxide. |
| 18. | Lead oxide. |
| 19. | Strontium oxide. |
| 20. | Mercury oxide. |
| 21. | Chromic acid. |
| 22. | Hydrogen peroxide - wet. |
| 23. | Sodium peroxydicarbonate. |
| 24. | Potassium peroxydicarbonate. |
| 25. | Metachloroperbenzoic acid. |
| 26. | Trifluroperacetic acid. |
| 27. | Trichloroperacetic acid. |
| 28. | Perbenzoic acid. |
| 29. | Potassium chromate. |
| 30. | Sodium chromate. |
| 31. | Sodium metaperiodate. |
| 32. | Potassium metaperiodate. |
| 33. | Copper oxide. |
| 34. | Cobalt oxide. |
| 35. | Osmium tetroxide. |
| 36. | Titaniuni dioxide. |
| 37. | Tungston oxide. |
| 38. | Diatomic halogens (iodine, chlorine, bromine and fluorine). |

In addition, there are numerous, more exotic agents that also effectively oxidize hydrogen sulfide (and mercaptans) in this device. These are indicated below (Table 4) and cross referenced with CAS numbers.

TABLE 4

Exotic oxidizers useful in this invention

| CHEMICAL | GAS # | CROSS-REF |
|---|---|---|
| tert-BUTYLPEROXY NEODECANOATE | [26748-41-4] | |
| tert-BUTYL PEROXYNEOHEPTANOATE | [26748-38-9] | |
| tert-BUTYLPEROXY OCTOATE | [13467-82-8] | tert-BUTYL PEROCTOATE |
| tert-BUTYL PEROXYPHENOXYACETATE | [0-0-0] | |
| 3-tert-BUTYLPEROXY-3-PHENYLPHTHALIDE | [25251-51-8] | |
| tert-BUTYLPEROXY PIVALATE | [927-7-1] | |
| tert-BUTYLPEROXY iso-PROPYL CARBONATE | [2372-21-6] | |

TABLE 4-continued

Exotic oxidizers useful in this invention

| CHEMICAL | GAS # | CROSS-REF |
|---|---|---|
| tert-BUTYLPEROXY STEARYL CARBONATE | [0-0-0] | |
| tert-BUTYLPEROXY o-TOLUATE | [22313-62-8] | |
| tert-BUTYLPEROXY-3,5,5-TRIMETHYLHEXANOATE | [13122-18-4] | |
| O,O-tert-BUTYL-O-iso-PROPYL PEROXYCARBONATE | [0-0-0] | |
| CHLOROPEROXYBENZOIC ACID | [0-0-0] | |
| 3-CHLOROPEROXYBENZOIC ACID | [937-14-4] | m-CHLOROPERBENZOIC ACID |
| 9(11),22-CHOLESTADIEN-24b-METHYL-5,8-PEROXY-3b-OL ACETATE | [0-0-0] | |
| 6,9(11),22-CHOLESTATRIEN-24b-METHYL-5,8-PEROXY-3b-OL ACETATE | [0-0-0] | |
| 6,9,(11),22-CHOLESTATRIEN-24b-METHYL-5,8-PEROXY-3b-OL ACETATE | [0-0-0] | |
| COPPER (II) OXYACETATE | [52503-63-6] | |
| COPPER OXYCHLORIDE | [1332-40-7] | |
| COPPER (II) OXYCHLORIDE | [1332-40-7] | COPPER OXYCHLORIDE |
| COPPER OXYCHLORIDE SULFATE | [0-0-0] | |
| TRIMETHYLCYCLOHEXANE | [6731-36-8] | 1,1-BIS(tert-BUTYLPEROXY)-3,3,5-TRIMETHYLCYCLOHEXANE |
| DICETYL PEROXY DICARBONATE | [26322-14-5] | |
| DICYCLOHEXYL PEROXY DICARBONATE | [1561-49-5] | |
| DI-2-ETHOXYETHYL PEROXYDICARBONATE | [52373-74-7] | |
| DI(2-ETHYLHEXYL)PEROXYDICARBONATE | [16111-62-9] | |
| 2,5-DIHYDROPEROXY-2,5-DIMETHYLHEXANE | [3025-88-5] | |
| 2,4-DIHYDROXY-2-METHYL-4-HYDROPEROXYPENTANE | [0-0-0] | |
| DIMETHOXY-iso-PROPYLPEROXYDICARBONATE | [0-0-0] | |
| 2,5-DIMETHYL-2,5-BIS(tert-BUTYLPEROXY)HEXANE | [78-63 7] | 2,5-DIMETHYL-2,5-DI(tert-BUTYLPEROXY)HEXANE |
| 2,5-DIMETHYL-2,5-BIS(tert-BUTYLPEROXY)HEX-3-YNE | [0-0-0] | |
| 2,5-DIMETHYL-2,5-BIS(2-ETHYLHEXOYLPEROXY)HEXANE | [13052-9-0] | 2,5-BIS(2-ETHYLHEXANOYLPEROXY-2,5-DIMETHYLHEXANE |
| 2,5-DIMETHYL-2,5-DI(BENZOYLPEROXY)HEXANE | [2618-77-1] | |
| 2,5-DIMETHYL-2,5-DI(tert-BUTYLPEROXY)HEXANE | [78-63-7] | |
| 2,5-DIMETHYL-2,5-Di(tert-BUTYLPEROXY)-3-HEXYNE | [1068-27-5] | 2,5-DIMETHYL-2,5-Di(tert-BUTYLPEROXY)HEXYNE-3 |
| 2,5-DIMETHYL-2,5-DI(tert-BUTYLPEROXY)HEXYNE | [0-0-0] | |
| 2,5-DIMETHYL-2,5-DI(tert-BUTYLPEROXY)HEXYNE-3 | [1068-27-5] | |
| 2,5-DIMETHYL-2,5-DI(2-ETHYLHEXANOYL PEROXY) HEXANE | [13052-9-0] | 2,5-BIS(2-ETHYLHEXANOYLPEROXY-2,5-DIMETHYLHEXANE |
| DI-(3-METHYL-3-METHOXY BUTYL)PEROXYDICARBONATE | [0-0-0] | |
| DIMYRISTYL PEROXYDICARBONATE | [53220-22-7] | |
| DI(PROPYL)PEROXYDICARBONATE | [16066-38-9] | |
| Di-iso-PROPYL PEROXYDICARBONATE | [105-64-6] | |
| ETHYL-3,3-BIS(tert-BUTYLPEROXY)BUTYRATE | [55794-20-2] | ETHYL 3,3-DI(tert-BUTYLPEROXY)BUTYRATE |

TABLE 4-continued

Exotic oxidizers useful in this invention

| CHEMICAL | GAS # | CROSS-REF |
| --- | --- | --- |
| ETHYL 3,3-DI(tert-BUTYLPEROXY)BUTYRATE | [55794-20-2] | |
| 2-ETHYLHEXYL PEROXYDICARBONATE | [1611-62-9] | |
| HYDROGEN PEROXY-SULFURIC UREA | [0-0-0] | |
| 1-[(1-HYDROPEROXYCYCLOHEXYL)DIOXY]CYCLOHEXANOL | [78-18-2] | |
| 1-HYDROPEROXYCYCLOHEXYL-1-HYDROXY CYCLOHEXYL PEROXIDE | [12262-58-7] | CYCLOHEXANONE PEROXIDE |
| 13(S)-HYDROPEROXYOCTADECA-9Z,11E-DIENOIC ACID | [33964-75-9] | |
| 13(S)-HYDROPEROXY-9Z,11E,15Z-OCTADECATRIENOIC ACID | [0-0-0] | |
| MAGNESIUM MONOPEROXYPHTHALATE | [84665-66-7] | |
| MAGNESIUM PEROXYPHTHALATE | [78948-87-5] | |
| MAGNESIUM PEROXYPHTHALATE HEXAHYDRATE | [0-0-0] | |
| MONOPEROXYPHTHALIC ACID, MAGNESIUM SALT | [78948-87-5] | |
| MONOPEROXYPHTHALIC ACID MAGNESIUM SALT HEXAHYDRATE | [84665-66-7] | |
| p-NITROPEROXYBENZOIC ACID | [943-39-5] | 4-NITROPERBENZOIC ACID |
| OXOPEROXYMOLYBDENUM(PYRIDINE)HEXAMETHYLPHOSPHORAMIDE | [23319-63-3] | OXOPIPEROXYMOLYBDENUM(PYRIDINE)HEXAMETHYLPHOSPHORAMIDE |
| OXOPIPEROXYMOLYBDENUM(PYRIDINE)HEXAMETHYLPHOSPHORAMIDE | [23319-63-3] | |
| PEROXYACETIC ACID | [79-21-0] | PERACETIC ACID |
| PEROXYDICARBONATE | [34099-48-4] | |
| PEROXYDISULFURYL FLUORIDE | [13709-32-5] | |
| PEROXYDOL | [0-0-0] | |
| PEROXYKETAL, CYCLIC | [0-0-0] | |
| PEROXYMONOSULFURIC ACID | [0-0-0] | |
| PEROXYNITRITE | [14042-1-4] | |
| PEROXYNITRITE, TETRAMETHYLAMMONIUM SALT | [157167-78-7] | |
| POTASSIUM PEROXYDIPHOSPHATE | [15593-49-4] | |
| POTASSIUM PEROXYDISULFATE | [7727-21-1] | POTASSIUM PERSULFATE |
| POTASSIUM PEROXY MONOSULFATE | [0-0-0] | |
| iso-PROPYL-sec-BUTYLPEROXYDICARBONATE | [0-0-0] | |
| SODIUM CARBONATE PEROXYHYDRATE | [0-0-0] | |
| SODIUM PEROXYCARBONATE | [4452-58-8] | |
| SODIUM PEROXYDISULFATE | [7775-27-1] | SODIUM PERSULFATE |
| TETRAKIS(PYRIDINE)SILVER(II) PEROXYDISULFATE | [15810-50-1] | |
| TETRAPOTASSIUM PEROXYDIPHOSPHATE | [0-0-0] | |
| 2,4,4-TRIMETHYLPENTYL-2-PEROXYNEODECANOATE | [0-0-0] | |
| 2,4,4-TRIMETHYLPENTYL-2- | [0-0-0] | |

TABLE 4-continued

Exotic oxidizers useful in this invention

| CHEMICAL | GAS # | CROSS-REF |
|---|---|---|
| PEROXYPHENOXYACETATE | | |
| VINYL TRIS(tert-BUTYLPEROXY)SILANE | [15188-9-7] | |

Yet a third type of material that can be reacted with hydro-sulfur compounds (hydrogen sulfide and mercaptans) can be referred to as "hydro-sulfur labile" compounds. These materials are organic substances possessing functional groups that can form products resulting form nucleophilic addition. For example, phthalic anhydride is effective at a level of one gram in a standard unit (see FIG. 6). Other organic functional groups that serve as hydro-sulfur labile compounds to react and convert the sulfur-containing malodorous components of flatus are indicated below:

TABLE 5

Hydro-sulfur labile converter functional groups

| | |
|---|---|
| 1. | Carboxylic acid anhydrides |
| 2. | Olefins |
| 3. | Alkynes |
| 4. | Carboxylic acid esters |
| 5. | Aldehydes |
| 6. | Isonitriles |
| 7. | Alkyl halides |
| 8. | Alpha diketones |
| 9. | Acyl halides |
| 10. | Diazo ketones |
| 11. | Epoxides |
| 12. | Isocyanates |
| 13. | Isothiocyanates |
| 14. | Thiocyanates |
| 15. | Vinyl ethers |
| 16. | Diazonium salts |
| 17. | Alpha-beta unsaturated carbonyls |
| 18. | Ketones |
| 19. | Alpha-beta unsaturated nitriles |
| 20. | Metal hydrides |
| 21. | Carbamates |

Interestingly, in addition to being capable of reacting with certain sulfur compounds, some of the reagents listed act as disinfectants as well. In particular, sodium dichloroisocyanuric acid and sodium hypochlorite have been proven to be effective for this purpose.

Figure 2:
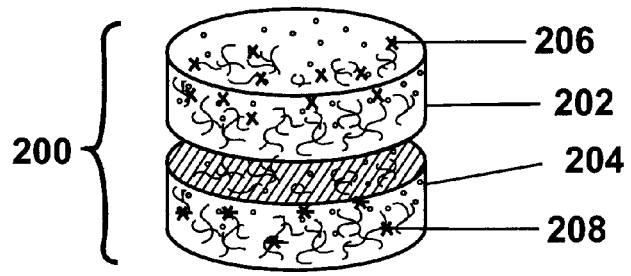
FIG. 2 is a perspective view of another embodiment of a two-tiered converter containing oxidizing agent, Lewis base and Lewis acid according to the invention.

For a more effective version of this appliance the carboxylic acid and amine (indoles and pyrroles) portions of flatus needed to be addressed as well. Activated charcoal can theoretically capture these materials. But unfortunately, the adsorbed species can be desorbed if the temperature in the room where the device is located should rise for any reason. Thus, as implied earlier, any device solely employing activated charcoal will end up emitting odor after a certain period of use. To avoid this, the carboxylic acids and amines, including ammonia from urination, must also be chemically converted to non-volatile substances rather than merely adsorbed. Unlike in the case of hydrogen sulfide and mercaptans, neither oxidation nor nucleophilic addition can be used for this purpose. However, carboxylic acids can be converted to non-volatile salts with a Lewis base. Analogously, the amines can be made into salts with a Lewis acid. But because Lewis acids and bases are not compatible, only one or the other can be impregnated along with the sulfur compound converter (Tables 3,4 and 5) on a single piece of converter fabric. Thus the need for separate agent-bearing zones. Thus, referring to FIG. 2, a version of the converter 200 that targets all malodorous components includes a laminar structure consisting of two layers of fabric 202, 204. Because the transformation of carboxylic acids and amines to their corresponding conjugate salts is a facile process, nearly any Lewis base 206 and nearly all Lewis acids 208 can be used. For strictly practical reasons readily available commodities are preferred. Thus, useful base converters include, but are not limited to, sodium carbonate, sodium bicarbonate, Calcite, potassium carbonate etc. Useful acid converters include ascorbic acid, aspartic acid, phenol, citric acid, maleic acid, oxalic acid succinic acid and so on.

During the course of developing this device, two secrets were discovered that marginally improved the effectiveness of the converter. The first was that when aqueous solutions of certain materials pre-adsorbed on a support (such as silica or others—vide supra) were mixed with select chemical converting reagents prior to being applied to the converter fabric, the performance of the converter was boosted. These materials (Table 6), referred to herein as "promoters," are linked by common features.

TABLE 6

Promoters used to enhance converter performance

| | |
|---|---|
| 1. | Tergitol$^R$ 9.5 from Union Carbide. |
| 2. | Alfonic$^R$ Nonionic from Vista Chemical Co. |
| 3. | JL 80X nonionic from Huntsman. |
| 4. | Polyethylene glycol. |
| 5. | Polypropylene glycol. |
| 6. | Glucan P-20 from Amerchol. |
| 7. | Cetyl range ethoxylated nonionic. |
| 8. | Lauryl range ethoxylated nonionic surfactant. |

The promoters cited are all water-soluble ethylene oxide or propylene oxide oligimers. They have inverse cloud points owing to their propensity to complex with water. Since solvent-solute kinetics are intrinsically more favorable than gas-solid kinetics, the enhanced performance is undoubtedly due to the presence of the bound water. In short, any water-soluble ethylene oxide or propylene oxide derivative, or mixtures of such, will have this beneficial effect to some degree, depending on the identity of the converter agents it is blended with and the degree to which it is capable of binding with water.

The second thing learned related to the use of activated charcoal. Even though it is not especially effectual when used by itself, some performance synergy is realized when it is used to complement the actual converter chemicals.

Figure 3:
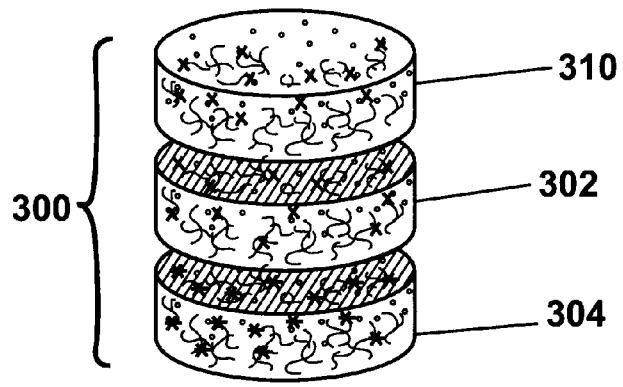
FIG. 3 is a perspective view of a three-tiered converter according to the invention.

Activated charcoal is not compatible with oxidizing agents, so the two cannot be blended together. But when a zone of charcoal is positioned upstream, it acts as a sort of holding reservoir for foul air components, which can release malodorous components to the converter chemicals at a later point in time. This is important in instances when the converter would otherwise be swamped by a heavy flux of malodorous air. Therefore, referring to FIG. 3, an adaptation of the two-tiered version of the converter includes a third tier carrying an activated charcoal. The three-tiered adaptation 300 therefore includes two fabric layers 302, 304, corresponding to the layers of FIG. 2, and an activated charcoal layer 310.

The converter fabric itself can be formed out of nearly any flexible cloth or mat material—including fordriniered pulp, woven, semi-woven, natural fiber, synthetic fiber, high rag content paper or felt, which is at least somewhat resistant to chemical degradation and is of sufficient porosity to allow a minimum air flow rate of 0.1 SCFM. This is true for two reasons: 1) the converter chemicals used are generally not especially reactive or harsh. 2) Any destructive aptitude they possess is severely modulated by their relatively low concentration. For example, half-inch nylon fiber mat with nominal 25-micron pore size works as well as one inch polypropylene fiber mat with 100-micron pore size. The number and kinds of different fabric materials (or porous beads in the case of a packed column arrangement) that can be successfully employed in fabricating the converter appears to be limitless.

2. Gas-handler

Figure 4:
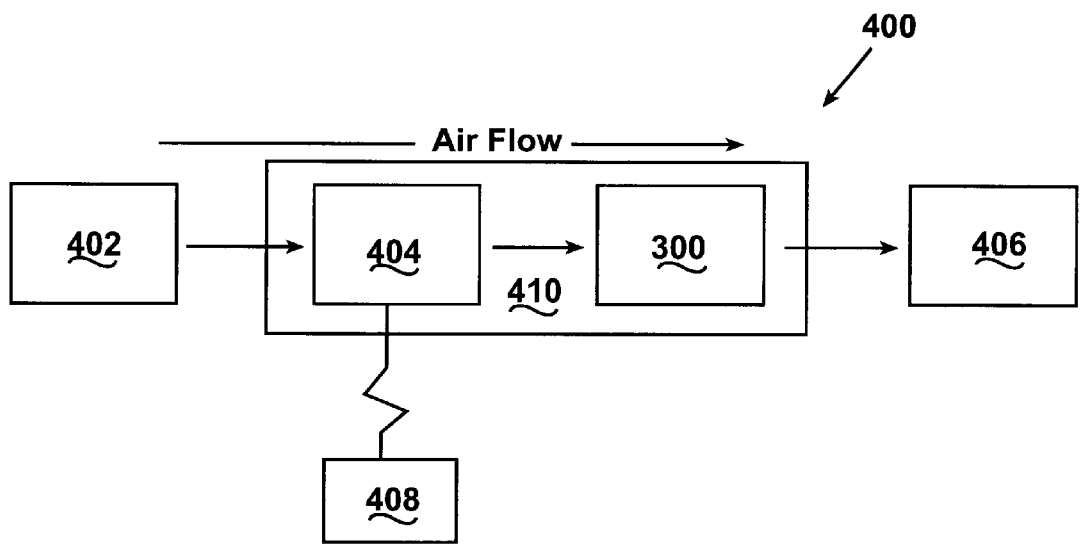
FIG. 4 is a schematic diagram of a foul air eliminator according to the invention.
Figure 5:
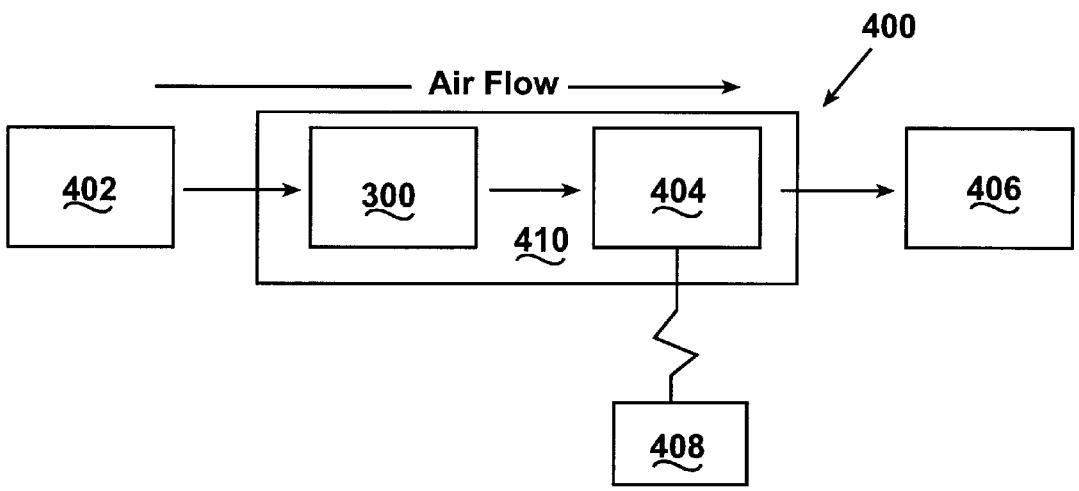
FIG. 5 is a schematic diagram of an alternative embodiment of a foul air eliminator according to the invention.

Referring now to FIGS. 4 and 5, the gas handling system is merely a collection of support elements required to channel malodorous gas to the converter so it can be made benign. Although some type of gas handling system is described in all prior art, in no case has it been connected to a chemical converter, which is essential to the successful operation of the appliance.

Specifically, the gas-handler 400 includes an intake 402, impeller 404, exhaust port 406, power source 408, and housing 410.

Housing 410 communicates between the intake 402 and the exhaust 406, carrying the impeller 404 and the converter 300, as depicted schematically (see FIG. 4). Since the only requirement is to deliver the malodorous air to the converter for alteration, there is an inherent flexibility in the way some of the elements can be arranged and scaled. For example, it matters not whether the impeller is positioned downstream from the converter (FIG. 5) or upstream from it (FIG. 4)—although in practice, the upstream location afforded better flow in most cases. Also, an enlarged version of the device accommodates more demanding applications. Use around bedpans in hospital rooms and in surgery rooms have been identified as areas where a larger version of this invention would be of value. In all these cases, however, the converter and all five elements of the gas-handling system are optimal. With the converter having already been explained, each element of the gas-handler will be discussed presently.

Figure 6:
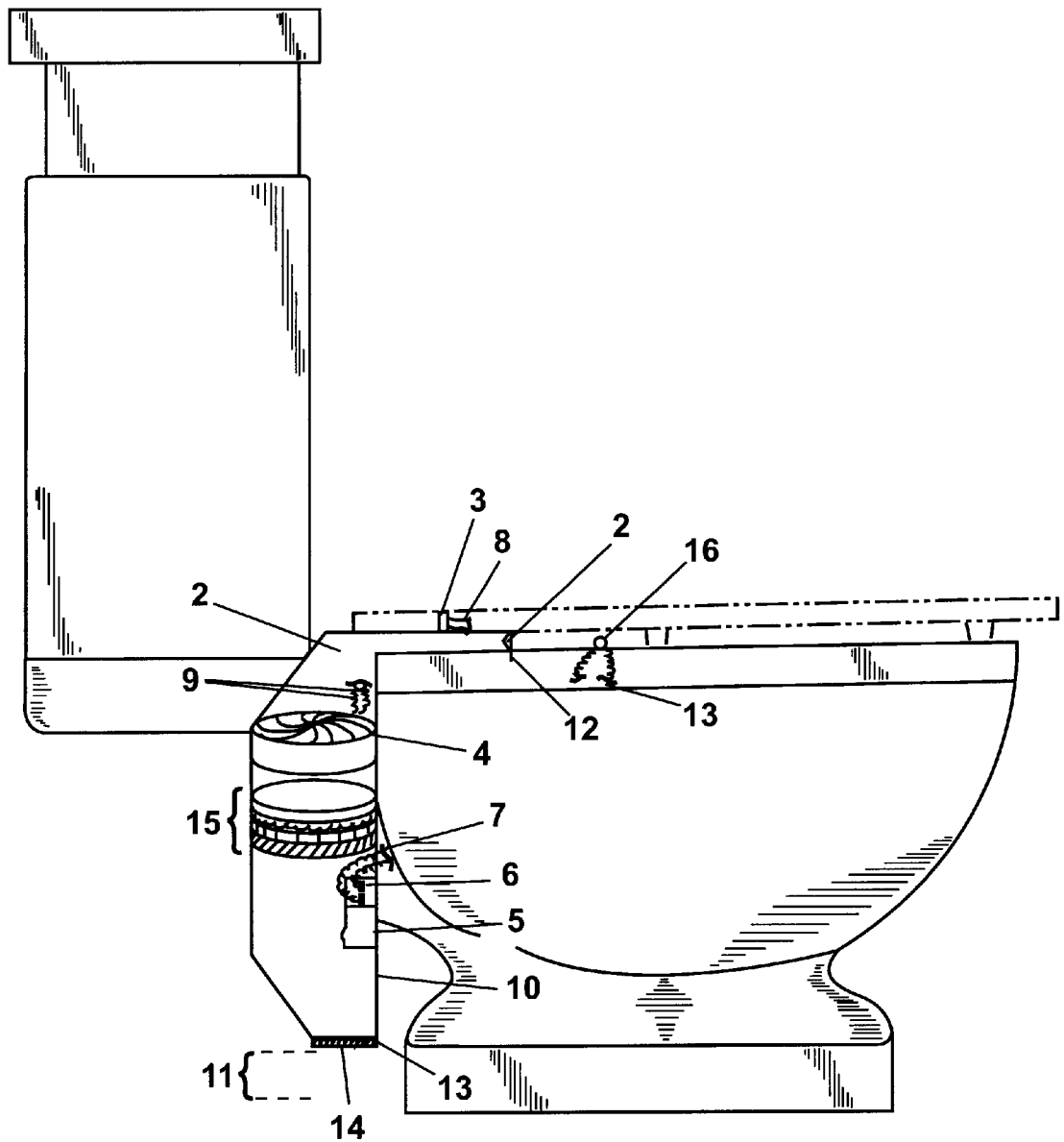
FIG. 6 is an elevational view of a foul air eliminator according to the invention.

In order for the converter to function properly, a majority of the malodorous gas must first be collected. This is accomplished by means of intake 402, including a port 1 leading to a hollowed flange 2 mounted on the sides and/or back of the toilet bowl during installation (FIG. 6). The intake port(s) 1, hollow flange 2 or combination thereof is the point of entry of the malodorous gas into the gas-handling system. In the case of a flush toilet they are located at or near the level of the toilet bowl rim. Air flow is generated by impeller 404. Owing to the relatively short distance the air travels, especially when the intake port 402 is mounted toward the back of the bowl, there is minimal flow resistance. Accordingly, the required flow rate is governed primarily by the volume of flatus to be removed during a single expulsion. Physiological data reveal that this volume is rarely greater than 300 ml (and more typically 150 ml). Furthermore, volume expansion resulting from movement to a lower pressure environment (~1 atm.) is not greater than 15%. From this data a volume of 200 ml can be established as a benchmark (i. e. applicable in >90% of the cases). When this is coupled with a factor for diffusion time (e. g. diatomic oxygen gas diffusion coefficient=0.178 cm2/ sec at 00 C), we arrive at a required flow rate of around 67 ml/sec. After converting units we get approximately 0.10 to 0.15 SCFM. Thus, 0.1 SCFM was computed as the minimum effective impeller flow rate for this invention.

It was learned that a large variety of impellers (fans, blowers and so on) were capable of efficiently delivering flow rates far in excess of 0.1 SCFM. Two-sided intake blowers were particularly attractive in experimental models owing to their shape. The impeller may be optionally activated by means of either a pressure sensitive actuator (set nominally for 20 pounds), or a manual control button. In either case the switch communicates with the power source and impeller (blower) through an electrical lead housed within the unit itself. In practice, impellers rated for around 20 SCFM were found to work well. The number of impellers commercially available that can deliver a flow rate in this neighborhood is staggering. Ones that have the following rating options all work satisfactorily in this invention:

| Parameter | Range |
| --- | --- |
| Flow, SCFM | .1–100 |
| RPMs | 100–5000 |
| Power, watts | 5–100 |
| Voltage | 3–240 |
| Current, amps | 0.2 min. |

The exhaust 406 is the opening by which the purified air escapes the handler 400 and reenters the room (FIG. 6). However, it is apparent that the escaping purified air possesses kinetic energy, which can theoretically be utilized. For example, a modular fragrance repository 14 can be placed at the exhaust port 406 so that the exhaust energy can be used to introduce a pleasant scent into the air during use of the invention. Though this appliance obviates the need for this option, its inclusion is prudent from a commercial standpoint.

The relatively diminutive flow rate requirements make it possible for power source 408 to be either a battery or a wall outlet (120 volt or 240 volt). It is housed within the unit itself in the case of the former. Model work demonstrates that a 12 volt battery can operate for six to eight weeks with regular daily use of this device before replacement is needed. Thus, there is considerable leeway for selecting sources of power to be incorporated into this invention. Independent of the source of power, the switch mechanism that activates whatever power source is in place can be selected from a variety of options. Among them are:

1. Pressure actuator switch
2. Manual switch
3. Infrared trigger type
4. Radio frequency type Flatus, though unpleasant, is neither hazardous nor corrosive. And since, by design, the chemical reagents housed in the converter never make direct contact with the gas-handling system, materials of construction of the gas-handler is not a troublesome issue. The only requirements are that they be machinable, semi-rigid to hold shape and have enough longevity to be practical. Therefore, a large array of materials can be used in fabricating this invention— including, but not limited to, the following:

1) Stainless steel
2) Aluminum
3) Carbon steel
4) PET
5) PVC
6) Polystyrene
7) High density polyethylene
8) LDPE
9) Polypropylene
10) Polycarbonate
11) ABS resin
12) Phenol formaldehyde resin
13) Wood
14) Particle laminate
15) Thermosetting resins
16) Thermoplastics
17) Polyvinyl actetate
18) Partially hydrolyzed polyvinyl acetate
19) Polyacrylonitrile
20) Polyacrylic ester
21) Caplan$^R$
22) Kevlar$^R$
23) Sheet metal In addition, the flexibility engendered by the overall invention design affords the potential of manufacturing all or portions of the gas-handling system by injection, or blow molding methodologies.

Referring to FIG. 6, the intake port 1 is located under the lid of the toilet. It communicates with the rest of the unit by means of the hollow flange 2. As the invention is being used, it may be activated by the manual switch 3. The foul air flows through the intake port and hollow flange by means of the pressure differential created by the in-line impeller 4. The impeller is a 3000 rpm, 20 SCFM blower powered with 11 Watts, by a 12 volt, 900 milliamp battery 5 through contacts 6 and leads 7. The battery also communicates with the manual switch 3 by means of the electrical leads 8. The impeller also communicates with the switch through the impeller leads 9.

The housing 10 is PVC. The overall length is 15 inches. The width is approximately 5.5 inches at its widest point. The battery is located near the bottom on the interior of the unit and is secured with adhesive and a truncated PVC flange just large enough to hold it. The flange extends laterally toward the center. It is positioned against one side so air flow is not obstructed. The unit sits up off the floor with a clearance 11 of approximately two inches. Its weight is supported by means of a hook-shaped fastener 12 that curves over and under the toilet bowl rim. The fastener 12 is an extension of the lower surface of the intake port. The exhaust port 13 is approximately six square inches and is fitted with a fragrance repository 14 composed of a scent absorbed onto a piece of porous felt that is roughly the same size as the exhaust port opening.

Turning now to the converter 15, the illustrated embodiment is the more advanced three-tiered version described earlier (FIG. 3) with a total lateral surface area of approximately 20 square inches. It is supported by means of an interior PVC lip that extends to the interior of the device toward the center. It is around 3/32 inches wide and runs along the entire interior circumference of the device at its widest point. The composition of the converter is as follows:

The first layer of the embodiment of the converter is a half-inch thick polypropylene fiber mat that is supporting 25 grams of 40 mesh activated charcoal.

The second layer of the converter in this embodiment is another half-inch thick piece of fiber mat impregnated with 75 grams of the following formula:

1. 15% Sodium dichloroisocyanuric acid.
2. 8% of 5% Sodium hypochlorite solution.
3. 18% Sodium bicarbonate (Lewis base).
4. 18% Alfonic$^R$ nonionic surfactant.
5. 39% Ultrasil$^R$ precipitated silica.
6. 2% Partially hydrolyzed polyvinyl acetate.

The third layer is yet another half-inch thick mat that was impregnated with 25 grams of the following formula:

1. 45% Citric acid.
2. 20% Alfonic$^R$ nonionic surfactant.
3. 35% Ultrasil$^R$ precipitated silica.

The top two layers rest on the bottom one, which is in turn supported by the PVC lip described earlier. This unit operated successfully for eight weeks before the battery required changing.

Example 2

Referring again to FIG. 6, an alternate embodiment has the intake port 1 located under the lid of the toilet. It communicates with the rest of the unit by means of the hollow flange 2. As the invention is used, it is activated by the pressure switch 16. The foul air flows through the intake port and hollow flange by suction created by the in-line impeller 4. The impeller was a 3000 rpm, 20 SCFM impeller receiving power from a 120 volt outlet (not shown). The power also communicates to the pressure switch by means of electrical leads 18. The impeller also communicates with the switch through the impeller leads 9.

The housing 10 is PVC. The overall length is 15 inches. The width is approximately 5.5 inches at its widest point. The battery is located near the bottom on the interior of the unit and is secured with adhesive and a truncated PVC flange just large enough to hold it. The flange extends laterally toward the center. It is positioned against one side so air flow is not obstructed. The unit sits up off the floor with a clearance 11 of approximately two inches. Its weight is supported by means of a hook-shaped fastener 12 that curves over and under the toilet bowl rim. The fastener 12 is an extension of the lower surface of the intake port. The exhaust port 13 is approximately six square inches and is fitted with a fragrance repository 14 composed of a scent absorbed onto a piece of porous felt that is roughly the same size as the exhaust port opening.

An alternative converter 15 is the simple one-layer design of FIG. 1 with a total lateral surface area of approximately 18 square inches. It is supported by means of an interior PVC lip that extends to the interior of the device toward the center. It is around 3/32 inches wide and runs along the entire interior circumference of the device at its widest point. The composition of the converter is as follows:

The mat is half-inch thick polypropylene fiber impregnated with 50 grams of the following formula:

1. 25% Calcium Oxide.
2. 10% of 5% Sodium hypochlorite solution.
3. 25% Alfonic$^R$ nonionic surfactant (Promoter).
4. 40% Ultrasil$^R$ precipitated silica.

This unit operated with fair success for a seven weeks.

Example 3

Referring again to FIG. 6, another embodiment has the intake port 1 located under the lid of the toilet. It communicates with the rest of the unit by means of the hollow flange 2. As the invention is being used, it is activated by the pressure actuator 16. The foul air flows through the intake port and hollow flange by means of the pressure differential created by the in-line impeller 4. The impeller is a 3000 rpm blower powered with 11 Watts, by a 12 volt, 900 milliamp battery 5 through contacts 6 and leads 7. The battery also communicates with the pressure switch 16 by means of the electrical leads 18. The impeller also communicates with the switch through the impeller leads 9.

The housing 10 is PVC. The overall length is 15 inches. The width is approximately 5.5 inches at its widest point. The battery is located near the bottom on the interior of the unit and is secured with adhesive and a truncated PVC flange just large enough to hold it. The flange extends laterally toward the center. It is positioned against one side so air flow is not obstructed. The unit sits up off the floor with a clearance 11 of approximately two inches. Its weight is supported by means of a hook-shaped fastener 12 that curves over and under the toilet bowl rim. The fastener 12 is an extension of the lower surface of the intake port. The exhaust port 13 is approximately six square inches and is fitted with a fragrance repository 14 composed of a scent absorbed onto a piece of porous felt that is roughly the same size as the exhaust port opening.

The third embodiment of the converter 15 is the two-tiered arrangement described earlier (FIG. 2) having total lateral surface area of approximately 20 square inches. It is supported by means of an double adhesive tape applied to the edge of the bottom layer. The first layer is one-inch thick nylon fiber mat impregnated with 85 grams of the following formula:

1. 19% Sodium dichloroisocyanuric acid.
2. 5% of 5% Sodium hypochlorite solution.
3. 16% Potassium carbonate (Lewis base).
4. 21% Alfonic$^R$ nonionic surfactant (Promoter).
5. 39% Ultrasil$^R$ precipitated silica.

The second layer is another half-inch thick polypropylene mat that was been impregnated with 25 grams of the following formula:

1. 50% Citric acid.
2. 20% Tergitol$^R$ nonionic surfactant.
3. 30% Ultrasil$^R$ precipitated silica.

This unit operated with excellent success for two and a half months.

Example 4

In another model all parameters were identical with those described in the first example with the following exceptions:

1. A 25 SCFM blower was substituted for the one described in the first example.
2. The exhaust port was not fitted with a fragrance repository.
3. The housing was straight-walled at the bottom rather being tapered.
4. The exhaust port was roughly twice as large.

Example 5

In yet another model all parameters were identical with those described in the second example with the following exceptions:

1. A 38 SCFM blower was substituted for the one described in the first example.
2. The housing was straight-walled at the bottom rather being tapered.
3. The exhaust port was roughly twice as large.

Example 6

In still another model all parameters were identical with those described in the first example with the following exceptions:

1. A 25 SCFM blower was substituted for the 20 SCFM blower described in the first example.
2. The exhaust port was not fitted with a fragrance repository.
3. The housing was straight-walled at the bottom rather being tapered.
4. The exhaust port was roughly twice as large.
5. 10% Potassium permanganate solution (5%) was added to the converter.
6. 13% Calcium oxide was added to the converter.
7. Sodium dichloroisocyanuric acid was not added to the converter chemical mixture.

Example 7

Figure 7:
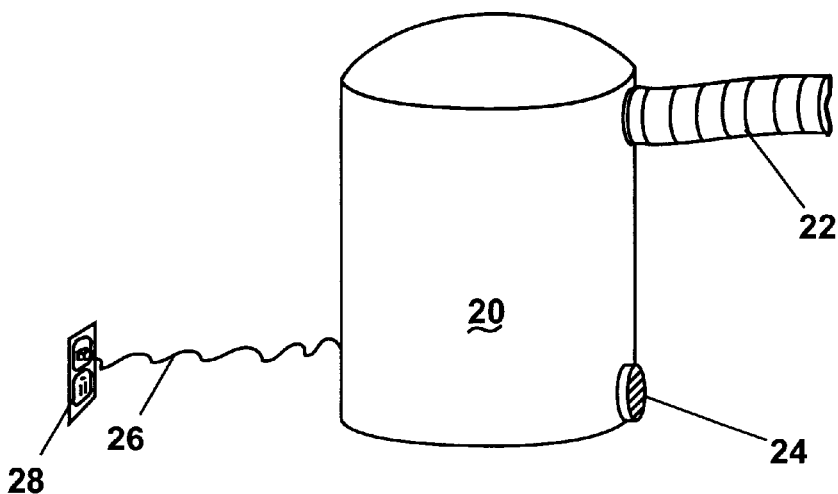
FIG. 7 is a perspective view of an alternate embodiment of a foul air eliminator according to the invention.

A "heavy duty" version 20 of the present invention is shown in FIG. 7. It is designed for use near hospital bed-pans and in operating rooms, was fabricated in a way that is conceptually identical to that described in the first example in the preferred embodiment, including an intake hose 22 and an exhaust port 24. This model differs only in the following ways:

1. It is dimensionally larger.
2. The in-line impeller is rated for 150 SCFM air displacement.
3. No fragrance repository is fitted in the exhaust port.
4. It is connected to a 120 volt electrical outlet 28 by connector 26.
5. The total weight of converter agent is 275 grams.
6. The unit was not tapered at the bottom.

Example 8

Figure 8:
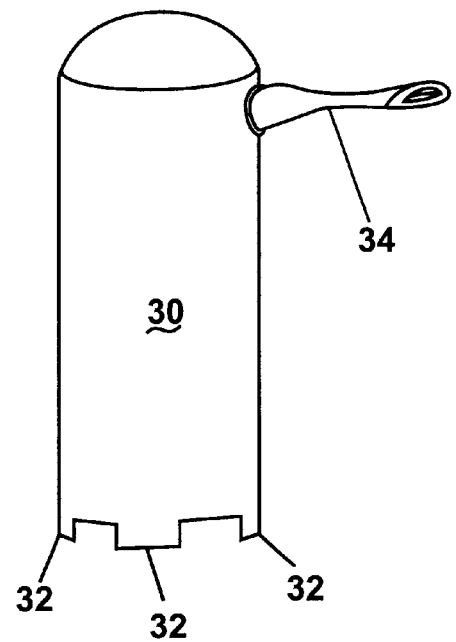
FIG. 8 is a perspective view of a further embodiment of the foul air eliminator according to the invention.

Another version of the present invention 30, shown in FIG. 8, rests on the floor rather than being supported by fastener 12 of FIG. 6. The floor model 30 is conceptually identical to that described in the first example in the preferred embodiment. This model differs only in the following ways:

1. It is straight-walled rather than tapered at the bottom.
2. It is supported by three one-inch high PVC legs 32.
3. It includes a hollow flange 34 formed as an oval where it intersects the housing.

Solving the chemistry is the precise approach which the present invention employs. Using a chemical converter, the malodorous components undergo a chemical metamorphosis to materials that are inoffensive to the sense of smell. Basically, it singles out the malodorous components and irreversibly captures and simultaneously converts these materials to substances that are not capable of being re-released into the air to generate the foul odor experience. Fortuitously, many of the materials, which work effectively as converters, also destroy bacteria. In addition, use of this invention obviates the need for using spray canisters, which can introduce CFCs (chloroflurocarbons) that have been cited as having a potentially harmful effect on atmospheric ozone.

While the invention has been specifically described in connection with certain specific embodiments thereof, it is to be understood that this is by way of illustration and not of limitation, and the scope of the appended claims should be construed as broadly as the prior art will permit.

What is claimed is:

1. A foul air converter comprising a first porous layer having an oxidizing agent or a hydro-sulfur labile compound in an amount sufficient to effectively react with malodorous compounds in air that is directed to pass through the converter, and an aqueous solution of a promoter carried by a support in a position to accelerate the reaction between the oxidizing agent or hydro-sulfur labile compound and the malodorous compounds when air is directed through the converter.

2. A foul air converter according to claim 1, wherein the support is adjacent to the first porous layer.

3. A foul air converter according to claim 1 wherein the support is in the first porous layer.

4. The converter of claim 1 wherein the aqueous solution of the promoter is adsorbed onto the support.

5. The converter of claim 1 wherein the oxidizer is adsorbed on a support.

6. The converter of claim 5 wherein the promoter and oxidizer are mixed on the porous layer.

7. The converter of claim 1 wherein the promoter is a water-soluble ethylene oxide of propylene oxide adduct.

8. The converter of claim 1 wherein the oxidizing agent is selected from dichloroisocyanuric acid or sodium hypochlorite.

9. The converter of claim 1 wherein the first porous layer further has one of a Lewis acid or a Lewis Base.

10. The converter of claim 1 further comprising a second porous layer having an activated charcoal.

11. The converter of claim 10 further wherein at least one of the porous layers has one of a Lewis acid or a Lewis Base.

12. The converter of claim 10 wherein the first porous layer has one of a Lewis acid or a Lewis base and the second porous layer has the other of a Lewis acid or a Lewis base.

13. The converter of claim 1 further comprising a second porous layer having one of a Lewis acid or a Lewis Base.

14. The converter of claim 9 further comprising a second porous layer having one of a Lewis acid or a Lewis Base.

15. The converter of claim 9 wherein the first porous layer has one of a Lewis acid or a Lewis base and the second porous layer has the other of a Lewis acid or a Lewis base.

16. The converter of claim 15 further comprising a third porous layer having an activated charcoal.

17. The converter of claim 16 wherein any two porous layers have one of a Lewis acid or a Lewis Base.

18. The converter of claim 17 wherein the third layer has one of a Lewis acid or a Lewis Base.

19. The converter of claim 1 wherein the first porous layer comprises any of a fabric, a felt, a woven or unwoven mat of chemically resistant fibers or filaments, and a column of beads.

20. A method of eliminating foul air from a confined space comprising:

gathering air containing malodorous compounds in a housing; and impelling the air through a converter in the housing, wherein the converter includes an oxidizing agent or a hydro-sulfur labile compound in an amount sufficient to effectively react with malodorous compounds in the air, and an aqueous solution of a promoter carried by a support in a position to accelerate the reaction between the oxidizing agent or hydro-sulfur labile compound and the malodorous compounds.

21. A method of making a foul air converter comprising:

selecting a porous layer from among a fabric, a felt, a woven or unwoven mat of chemically resistant fibers or filaments, and a column of beads;

selecting an oxidizer;

adsorbing an aqueous solution of a promoter onto a support;

applying the oxidizer to the porous layer, wherein the oxidizer is in an amount sufficient to effectively react with malodorous compounds in air; and positioning the support where the promoter will accelerate the reaction between the oxidizing agent or hydro-sulfur labile compound and malodorous compounds.

22. The method of claim 21 wherein the promoter is selected from a water-soluble ethylene oxide or propylene oxide adduct.

23. The method of claim 22 wherein the oxidizer is selected from dichloroisocyanuric acid or sodium hypochlorite.

24. A foul air converter comprising a first porous layer having an oxidizing agent or a hydro-sulfur labile compound in an amount sufficient to effectively react with malodorous compounds in air passing through the converter, and further having an aqueous solution of a promoter adsorbed onto a support to accelerate the reaction between the oxidizing agent or hydro-sulfur labile compound and the malodorous compounds.

25. The converter of claim 24 wherein the promoter and oxidizer are mixed on the first porous layer.

26. The converter of claim 24 wherein the support comprises silica.

27. The converter of claim 24 wherein the first porous layer further has one of a Lewis acid or a Lewis Base.

28. The converter of claim 24 further comprising a second porous layer having an activated charcoal.

29. A foul air eliminator comprising an intake port, an exhaust port, an impeller, a power source, and a converter, wherein the impeller, driven by the power source, will deliver air containing malodorous compounds from the intake port to the exhaust port through the converter, and wherein the converter includes an oxidizing agent or a hydro-sulfur labile compound in an amount sufficient to effectively react with the malodorous compounds, and wherein the converter further includes an aqueous solution of a promoter carried by a support in a position to accelerate the reaction between the oxidizing agent or hydro-sulfur labile compound and the malodorous compounds when air is directed to pass through the converter.

* * * * *

UNITED STATES PATENT AND TRADEMARK OFFICE
CERTIFICATE OF CORRECTION

PATENT NO. : 6,528,014 B1
DATED : March 4, 2003
INVENTOR(S) : Stephen L. Parkhurst et al.

It is certified that error appears in the above-identified patent and that said Letters Patent is hereby corrected as shown below:

Column 3,
Lines 15-47, should be replaced with:
  -- The invention lies in a foul air converter having a first porous layer that includes an oxidizing agent or a hydro-sulfur labile compound in an amount sufficient to react with malodorous compounds in air that is directed through the converter. An aqueous solution of a promoter is carried by a support in a position to accelerate the reaction between the oxidizing agent or hydro-sulfur labile compound and the malodorous compounds when air is directed through the converter. The support can either be adjacent to or in the first porous layer.

Preferably, the aqueous solution of the promoter is adsorbed onto the support. In addition, the oxidizer can be adsorbed on to the support. The promoter and the oxidizer can even be mixed on the first porous layer.

In one aspect of the invention, the promoter is a water-soluble ethylene oxide or propylene oxide adduct. The oxidizing agent is typically selected from dichloroisocyanuric acid or sodium hypochlorite. As well, the first porous layer can have either a Lewis acid or a Lewis base. The support can be silica.

In a further aspect of the invention, the converter can have a second porous layer with activated charcoal. In this case, the Lewis acid or the Lewis base can be in the second porous layer. Of course, a Lewis acid can be in one porous layer and a Lewis base in the other. In yet another aspect, the converter can have a third porous layer with the activated charcoal, the second having either a Lewis acid or a Lewis base. Typically, the first porous layer in any embodiment will comprise felt, fabric, a woven or unwoven mat of chemically resistant fibers, or a column of beads.

Another aspect of the invention comprises a method of eliminating foul air from a confined space. In the method, air containing malodorous compounds is gathered in a housing, and then the air is impelled through a converter. The converter has an oxidizing agent or a hydro-sulfur labile compound in an amount sufficient to react with the malodorous compounds, and an aqueous solution of a promoter carried by a support

UNITED STATES PATENT AND TRADEMARK OFFICE
CERTIFICATE OF CORRECTION

PATENT NO. : 6,528,014 B1
DATED : March 4, 2003
INVENTOR(S) : Stephen L. Parkhurst et al.

It is certified that error appears in the above-identified patent and that said Letters Patent is hereby corrected as shown below:

Column 3 (cont'd),
in a position to accelerate the reaction between the oxidizing agent or hydro-sulfur labile compound and the malodorous compounds.

Also covered by the invention is a method of making a converter. In this method, a porous layer is selected from among fabric, felt, a woven or unwoven mat of chemically resistant fibers or filaments, and a column of beads. An oxidizer is selected and an aqueous solution of a promoter is adsorbed onto a support. The oxidizer is applied to the porous layer in an amount sufficient to effectively react with malodorous compounds in air; and the support is positioned where the promoter will accelerate the reaction between the oxidizing agent or hydro-sulfur labile compound and the malodorous compounds. --

Column 19,
Line 66, "oxide of propylene" should be -- oxide or propylene --

Signed and Sealed this

Thirtieth Day of December, 2003

JAMES E. ROGAN
*Director of the United States Patent and Trademark Office*